(12) United States Patent
Fulbrook (10) Patent No.: US 11,452,793 B1
(45) Date of Patent: Sep. 27, 2022

(54) ULTRAVIOLET DISINFECTING CARTRIDGE SYSTEM

(71) Applicant: Jim E. Fulbrook, Fairfax, VA (US)

(72) Inventor: Jim E. Fulbrook, Fairfax, VA (US)

( * ) Notice: Subject to any disclaimer, the term of this patent is extended or adjusted under 35 U.S.C. 154(b) by 0 days.

(21) Appl. No.: 17/599,287

(22) PCT Filed: May 17, 2021

(86) PCT No.: PCT/US2021/032776
§ 371 (c)(1),
(2) Date: Sep. 28, 2021

(87) PCT Pub. No.: WO2021/236525
PCT Pub. Date: Nov. 25, 2021

Related U.S. Application Data

(60) Provisional application No. 63/026,003, filed on May 16, 2020.

(51) Int. Cl.
*A61M 16/06* (2006.01)
*A61L 9/20* (2006.01)
*A61M 16/10* (2006.01)
*A61M 16/08* (2006.01)

(52) U.S. Cl.
CPC ............ *A61L 9/205* (2013.01); *A61M 16/06* (2013.01); *A61M 16/0816* (2013.01); *A61M 16/10* (2013.01); *A61L 2209/11* (2013.01); *A61L 2209/12* (2013.01)

(58) Field of Classification Search
CPC ....... A41D 13/1146; A42B 3/288; A61L 9/16; A61L 9/20; A61L 9/22; A61M 15/02; A61M 16/00; A61M 16/0009; A61M 16/0051; A61M 16/0054; A61M 16/0069; A61M 16/0081; A61M 16/024; A61M 16/06; A61M 16/0683; A61M 16/08; A61M 16/105; A61M 16/1055; A61M 16/1065;
(Continued)

(56) References Cited

U.S. PATENT DOCUMENTS

3,126,003 A * 3/1964 Steel .................... A61M 15/02
604/23
3,744,216 A * 7/1973 Halloran ................ B03C 3/155
55/315
(Continued)

*Primary Examiner* — Annette Dixon
(74) *Attorney, Agent, or Firm* — Invention To Patent Services; Alex Hobson (57) ABSTRACT

An ultraviolet disinfecting cartridge system utilizes an ultraviolet disinfecting cartridge particularly adapted for coupling with a face mask that covers the nose and mouth or to the inhale and exhale tubing of a patient ventilator. The ultraviolet disinfecting cartridge includes multiple UV light emitters that emit UVGI light into the flow channel of the cartridge to neutralize or destroy pathogens. A plurality of baffles may be configured in the flow channel to create a serpentine airflow to increase pathogen exposure time to UV light. A photocatalyst material such as titanium oxide may be configured within the flow channel that is activated by UV light to increase disinfection. An ionizer may be configured proximal to the inlet to produce charged particles that provide disinfection. Any ozone produced may be mitigated by a catalytic converter to a safe level. Inlet and outlet filters may be detachably attachable to the ultraviolet disinfecting cartridge.

13 Claims, 4 Drawing Sheets

(58) Field of Classification Search
CPC .............. A61M 16/107; A61M 16/202; A61M 16/208; A61M 16/22; A61M 2016/0021; A61M 2016/0036; A61M 2016/102; A61M 2016/1025; A61M 2202/0476; A61M 2205/0238; A61M 2205/125; A61M 2205/587; A61M 2205/8212; A61M 2205/8237; A61M 2209/06; A62B 18/04; A62B 29/00; B01D 45/04; B01D 46/10; B01D 50/00; B03C 3/155; F24F 3/16; Y10S 128/913; Y10S 55/35
See application file for complete search history.

(56) References Cited

U.S. PATENT DOCUMENTS

| | | | | |
|---|---|---|---|---|
| 4,676,236 A | * | 6/1987 | Piorkowski | A62B 18/04 |
| | | | | 128/201.25 |
| 5,165,395 A | * | 11/1992 | Ricci | A41D 13/1146 |
| | | | | 55/DIG. 35 |
| 6,041,777 A | * | 3/2000 | Faithfull | A61M 16/0054 |
| | | | | 128/200.24 |
| 6,233,748 B1 | * | 5/2001 | Gieger | A62B 29/00 |
| | | | | 128/205.27 |
| 8,252,100 B2 | * | 8/2012 | Worrilow | B01D 46/521 |
| | | | | 55/482 |
| 11,191,864 B1 | * | 12/2021 | Singal | A61M 16/0683 |
| 2006/0169141 A1 | | 8/2006 | Yuen | |
| 2006/0283786 A1 | | 12/2006 | Harbers | |
| 2007/0163588 A1 | * | 7/2007 | Hebrank | A61M 16/0069 |
| | | | | 128/205.29 |
| 2008/0019861 A1 | | 1/2008 | Silderhuis | |
| 2011/0083670 A1 | | 4/2011 | Walacavage | |
| 2011/0272595 A1 | * | 11/2011 | Neister | A61L 9/22 |
| | | | | 250/435 |
| 2017/0100496 A1 | | 4/2017 | Shur et al. | |
| 2019/0117820 A1 | | 4/2019 | Dam | |
| 2019/0240370 A1 | | 8/2019 | Benedek et al. | |
| 2021/0330851 A1 | * | 10/2021 | Bell | A41D 13/1192 |

\* cited by examiner

ULTRAVIOLET DISINFECTING CARTRIDGE SYSTEM

CROSS REFERENCE TO RELATED APPLICATIONS

This application is a national stage application of PCT/US2021/032776, filed on May 17, 2021, which claims the benefit of priority to U.S. patent application Ser. No. 63/026,003, filed on May 16, 2020; the entirety of both applications are hereby incorporated by reference herein.

BACKGROUND OF THE INVENTION

Field of the Invention

The invention relates an ultraviolet (UV) disinfecting cartridge system comprising an ultraviolet light and ionizing disinfecting cartridge particularly adapted for coupling with a ventilator system, such as to a patient ventilator, along the inhale and exhale ventilator hoses and/or to a face mask that covers the nose and mouth that disinfects ambient air that is drawn through the disinfecting cartridge as an active personal protective equipment (PPE) system that destroys pathogens such as COVID-19 and prevents the spread of pathogens.

Background

The COVID-19 pandemic has created urgent needs and requirements in Personal Protective Equipment (PPE) such as wearable systems that include face masks, face shields, and ventilators to include patient ventilator systems for severely ill patients in healthcare facilities. Current PPE and patient ventilator systems provide some level of "passive" protection primarily as barriers; whereas "active" PPE provides a significant level of disinfection through such means as exposure to Ultraviolet (UV) light, an ionization system, and to ozone to achieve an operationally defined and statistical disinfection lethality on the order of 99.9% or higher effectiveness. PPE systems also include gowns, gloves, and other wearable or hospital devices.

Face masks and face shields are standard PPE that healthcare workers and first responders use to provide protection to the face, nose and mouth and are considered passive PPE that provide barriers to pathogens. However, air can move around and fiber masks that cover the nose and mouth still allow some moisture to pass through them during breathing when worn. Pathogens primarily transmit to a person by surviving in water droplets. Passive masks do not provide disinfection; that is, they do not destroy pathogens by some active means.

Patient ventilators are used to help critically ill individuals to breathe, such as those having influenza or other viruses, such as COVID-19. The ventilators are reused for one patient and then for another, which requires that they be effectively disinfected to avoid or lessen the risk of cross contamination between patients if the tubing and ventilation systems are not disinfected.

Pathogens such as viruses, bacteria, and fungi are transmitted through the air or by touching an infected surface or object that contaminates the person's hand, which can then infect the person if they touch their mouth, nose, eyes, an open wound, or other anatomical orifice. The world pandemic caused by the virus COVID-19 is attributed to the spread of the pathogen primarily through airborne water droplets and by surface transmission through the transfer process as described. To prevent the spread of pathogens, people are encouraged to wear PPE when they are around other people and to regularly and thoroughly wash their hands to remove or destroy pathogens therefrom. The use of disinfecting chemicals is another means to control infectious diseases on surfaces and aerosols provide some protection from airborne pathogens, but the protection is incomplete or temporary and not continuous, which is required for effective disinfection and protection.

UV light has been shown to be an effective disinfecting agent in preventing and controlling infectious diseases. Numerous studies demonstrate that UV light in a certain wavelength range is highly effective in attaining a 99.9% disinfection rate, which is based on the power of the UV source (amount of UV photons emitted), the wavelength of the UV source, the proximity and dispersion of the UV light to the pathogens, the amount of exposure time based on the airflow, and the combination of these variables.

UV light is absorbed by molecular bonds typically in the genetic structures of the pathogen that either alter the structure, which is called neutralizing, or the UV light destroys the pathogen by breaking the molecular bond, both of which render the pathogen non-infectious. For UV light to be effective, it must be exposed to pathogens for a period of about one tenth of a second or less based on the rate constant variables to destroy pathogens in that volume of air.

There are numerous UV light systems used for disinfection in the market, but they are usually industrial and cover large volumes of air and surfaces or there are individual hand-held and wand-like systems that only use one UV wavelength source to disinfect smaller surface areas and air volumes. Such systems often do not provide adequate coverage to disinfect pathogens in the air or on the surface of objects at or above a 99.9% level.

There is a distinction between disinfection and sterilization that should not be confused, wherein the term "sterilization" means that 100% of pathogens are destroyed, which happens only under very stringent conditions and only lasts for a short period of time once the sterilized objects are exposed to air, and wherein disinfection means some percentage of pathogens are destroyed or neutralized. Note also that pathogens are often confused with allergens.

All energy occurs on what is called the "Electromagnetic Spectrum", which is defined by the wavelength of the energy unit from very large (meters) to very small (Angstroms). Within this spectrum there are the ranges of Infrared light (wavelengths above 700 nanometers (nm) to over 1,000 nm in size), visible light (700-400 nm), and Ultraviolet light (400-100 nm). Units of energy in these light ranges are called photons. The shorter the wavelength, the higher the energy within the photon. Hence, UV light is much more powerful than visible light and it has the ability to bend or break molecular bonds in structures within living cells when absorbed. Life on Earth evolved based on these energy ranges and their abundance on the earth's surface, as the primary source of these energies is the sun. Fortunately, the atmosphere absorbs some wavelengths that can be harmful such as UV light.

UV light is generally broken down into three bands based on the nanometer wavelength. UVA occurs at 400-320 nm, UVB occurs at 320-280 nm, and UVC occurs at 280-200 nm. UV light from 200-100 nm is absorbed instantly in the atmosphere so it is not relevant to discuss further. Below UV on the electromagnetic spectrum are gamma and x-rays that are well known for their ability to be harmful and damaging to life in general if exposed in anything other than very low doses. UVA and UVB light penetrate the Earth's atmosphere and are abundant on the surface. These rays are beneficial for the synthesis of Vitamins A and D in many organisms, but in higher doses these light rays are harmful and can cause erythema (sunburn) and skin cancers in humans.

The term "Germicidal Irradiation" is given to those UV wavelengths in the UVC range that are effective at disinfecting pathogens. UVA is not germicidal, UVB is somewhat germicidal, but not at levels that readily achieve the goal of 99.9% disinfection, and UVC light at 200-280 nm is defined as the Ultraviolet Germicidal Irradiation (UVGI) range. In this invention, only UVGI emitting sources are being used. Hence, the general term of UV used in this application is referring to UVGI light. UVGI light can come from numerous sources, but this invention will only be using Light Emitting Diodes (LEDs) that are defined by the dominant wavelength they emit. Many UV LEDs in the market are tunable and generally have narrow band ranges. Research has shown that for the broad range of UVGI light, LEDs with dominant emittances in the range of about 250-280 nm and about 210-230 nm are most effective for disinfection.

Research has also shown that the 250-280 nm range is most effective for "destroying" pathogens by breaking molecular bonds such that scientists have been able to identify the specific bonds in given pathogens that are most vulnerable (more easily absorb the UV light leading to its alteration). The UVGI in the range of 210-230 nm is interesting, especially at the narrow range of about 222 nm where the resonant energy is readily absorbed by specific molecular bonds, but these bonds are typically "conformed" or changed in shape and not broken so that the DNA/RNA/protein structure is "neutralized" and no longer effective at its function, which for pathogens such as viruses is replication within the cells of infected individuals. Alternate UVC/UVGI wavelengths may be used if proven effective.

The narrow range 222 nm light has also been shown to be unique in that it generally does not penetrate the skin on humans below the epidermal surface where only dead skin occurs, and the 222 nm light does not penetrate the external surfaces of the eyes as well. In effect, the 222 nm narrow band LEDs are recognized as being relatively safe for human users, although all UVGI light should be considered harmful where proper safety precautions are observed. In this novel invention, the disinfecting cartridge system is designed to safely block and absorb stray UV light so regardless of the wavelength, the embodiments described herein are safe for users from UV exposure, and the air that flows through the system will also be safe to breathe and free of any infectious pathogens.

SUMMARY OF THE INVENTION

The invention is directed to an ultraviolet disinfecting cartridge system comprising an ultraviolet disinfecting cartridge particularly adapted for coupling with a wearable PPE face mask or a patient ventilator where cartridges are inserted into the inhale hose and/or exhale hose of the system. An exemplary ultraviolet disinfecting cartridge may be configured to couple with a face mask and have an inlet to outside air with a fan to provide continuous and measured airflow through the cartridge tube to an outlet coupled with the face mask. An exemplary ultraviolet disinfecting cartridge configured for coupling with a face mask, to produce a UV disinfecting face mask system, may have a linear or straight cartridge or a serpentine UV disinfecting cartridge having two or more 180-degree turns or other type of serpentine design so that the cartridge is compacted closer to the face mask attachment rather than being elongated. A serpentine UV disinfecting cartridge may have a better weight distribution and be more ergonomic in design.

An exemplary ultraviolet disinfecting cartridge may include an inlet adapter for coupling with a ventilator hose and an outlet adapter for coupling with another ventilator hose before it attaches to a ventilator face mask on the breathing or inhale hose, or tubing. An exemplary ultraviolet disinfecting cartridge may have another similar inline cartridge system inserted into the exhale tubing of a patient ventilator so that potentially infectious exhaled air from the patient is disinfected. Other persons in the room will not be exposed to viable pathogens and a special positive pressure hospital room ventilation system is not required.

The ultraviolet disinfecting cartridge includes UV light emitters that emit UV light into the airflow channel of the ultraviolet disinfecting cartridge to disinfect breathing air through neutralizing and/or destroying pathogens. The ultraviolet disinfecting cartridge may comprise a plurality of baffles that create a serpentine flow of the breathing air to increase the resonance time of exposure to UV light. The surface of the baffles may be made from a material that reflects UV light but that is also irregular. For instance, flat baffles that are dimpled over the surface create a more random dispersion of the reflected UV light, which has been shown to increase photon capture by pathogens, and thus increase lethality. In addition, an exemplary ultraviolet disinfecting cartridge may include a reactive material within the flow channel, such as being coated onto the inside surfaces of the flow channel that is configured to react with organic and molecular compounds such as ozone. An exemplary reactive material may be a photocatalyst, such as titanium dioxide, that is activated in the presence of UV light to absorb it, which would be useful at the end of the cartridge tube to eliminate stray UV light from exiting the tube.

An exemplary ultraviolet disinfecting cartridge may include baffles that produce a serpentine or tortuous flow through the flow channel. The baffles may be configured in an alternating configuration from either side of the flow channel, thereby making the flow of air travel back and forth as it progresses along the length of the flow channel. In an exemplary embodiment, the baffles are configured substantially orthogonal to the length axis of the flow channel. The baffle may also be a spiraling baffle producing a spiraling flow of air through the cartridge. The flow of air, either breathing air or exhalation air, may flow back and forth between the alternating baffles. The flow channel may have a length that is effective to neutralize or destroy pathogens. The length of the ultraviolet disinfecting cartridge system, or flow channel may be determined through testing to ensure that the number and intensity of the UV lights coupled with the ionizer effects within the cartridge neutralize or destroy a measured 99.9% of the pathogens passing through the system.

The length of the ultraviolet disinfecting cartridge system, or flow channel may be about 10 cm or more, about 12 cm or about 15 cm or more, about 20 cm or more and any length between and including the length values provided. The flow channel may include two or more baffles, such as about four or more baffles, about six or more baffles, about ten or more baffles, about 20 or more baffles and any range between and including the number of baffles listed. The baffles may be configured to produce orthogonal flow channels, or flow channels between the baffles that extend substantially orthogonal to the length axis. UV light emitters may be configured to emit UV light into the flow channel between the baffles.

In an exemplary ultraviolet disinfecting cartridge, the UV light emitter may emit light along the length of the flow channel and/or may be configured to emit light orthogonally to the length axis. The UV light emitters may be configured along the wall of the flow channel and emit UV light across the flow channel, or orthogonally. In an exemplary embodiment, a UV light emitter is configured to emit UV light into a baffle flow channel, or flow channel produced between the baffles, such as into an orthogonal flow channel produced by these baffles. A baffle flow channel may have UV light being emitted from opposing ends of the baffle flow channel, wherein the light from a first end is incident on the light emitter on the opposing second end. In this way, the airflow in the baffle flow channel is getting a higher dose of UV light.

An exemplary ultraviolet disinfecting cartridge may include any suitable number of UV light emitters, such as one or more, four or more, about eight or more, about ten or more, about 20 or more, about thirty or more and any range between and including the values provided. An exemplary ultraviolet disinfecting cartridge may include airflow louvers or a screen at the entry that further prevents UV light from escaping out the one end and it may have a fiber filters on each end of the flow channel that also prevents any UV light from escaping outside of the system.

The UV light emitters may be configured to produce Ultraviolet Germicidal Irradiation (UVGI) light that neutralizes or destroys pathogens. UVGI light in the range of about 200-280 nm is operationally defined as UVGI because research has shown that this range of UV light photons are most effective for disinfection by neutralizing and/or destroying pathogens to include viruses, bacteria, fungi, and other micro-organisms. Two or more UVGI dominant, narrow-band wavelength light emitting diode (LED) emitters may be used such as 220 +/−5 nm and 250-280 nm (265 +/−15 nm) in the cartridge system. These emitters may be controlled so that one, the other, or both are illuminated during use. If only one wavelength emittance is used, the power of the UV LEDs may be increased to offset the reduction of UVGI light from the other wavelength LEDs.

An exemplary ultraviolet disinfecting cartridge may include an ionizer that is configured proximal to the inlet to produce disinfecting ionization of particulate matter and pathogens in the airflow channel and may produce a minimal amount of ozone, which is also known to react with organic and molecular compounds, and is an effective disinfectant to pathogens in the breathing air and/or exhalation air. The ionizer may produce a level of ozone that is safe for inhalation or the ultraviolet disinfecting cartridge may include a catalytic material to react with the ozone to reduce the concentration before inhalation, or substantially remove the ozone to no more than about 1.0 ppm, no more than about 0.5 ppm, no more than about 0.25 ppm and preferably no more than about 0.1 ppm. An ionizer may turn off during inhalation and on during exhaling or reduce the concentration of ozone that is produced during inhaling. An ultraviolet disinfecting cartridge may include an inlet HEPA filter and/or outlet HEPA filter that are detachably attachable to the ultraviolet disinfecting cartridge. A UV disinfecting cartridge may become part of a face mask when it is coupled with a wearable system that covers the nose and mouth of a person working with infectious patients.

An exemplary ultraviolet disinfecting cartridge may include an ionizer to produce an amount of ionization and ozone gas that may react with pathogens to neutralize and/or destroy them. An exemplary ionizer produces an amount of ozone as a by-product, not as the primary disinfectant. UVGI also produces some amount of ozone gas by-product as well. A plate ionizer emits charged particles and then collects them on plates at the end of the airflow tube. Plate ionizers typically emit low levels of ozone that meet the 0.05 ppb standard to be safe for inhaling. The collecting plates may be detachably attachable and require cleaning periodically to remove a buildup of ionized particulate matter. An ionizer emitter may be configured proximal to the cartridge tube inlet. An ionizer configured proximal to the inlet will produce ozone that is carried with the breathing air through the flow channel. The ozone may react with organic compounds and pathogens to disinfect the breathing air in the ultraviolet disinfecting cartridge. Also, an ionizer may disinfect the exhalation air as well.

In an exemplary embodiment, an ionizer is configured to produce a level of ozone that is safe for inhaling. In another embodiment, an ionizer produces a level of ozone that is reduced by a reactive material configured in the ultraviolet disinfecting cartridge tube at the end closest to the user's face. The reactive material may be an ozone reactive catalyst such as manganese dioxide, which may react by absorbing ozone prior to inhaling to reduce the concentration to a safe level, which as stated, is about 0.05 ppb to be safe for human inhalation. People vary in how ozone may affect them, as some people react negatively, while others appear to have little or no effects from low levels of ozone. An ionizer may be configured to operate only when the flow of air is exhalation air, thereby further reducing or preventing inhaling any ozone. A controller on the outside of the UV disinfecting cartridge may turn the ionizer on or off as desired by the user.

An exemplary ultraviolet disinfecting cartridge system may include a reactive material configured in the ultraviolet disinfecting cartridge, such as titanium dioxide that is photocatalytic in the presence of UV light and increases the reactivity with pathogens to further increase its lethality. Titanium dioxide is an example of a photocatalyst as other known photocatalysts may be used in the ultraviolet disinfecting cartridge to react with pathogens. A reactive material may be coated onto the interior of the ultraviolet disinfecting cartridge including the inside surface walls and the baffle surfaces.

An exemplary ultraviolet disinfecting cartridge system may include a reactive material configured at the outlet end in the ultraviolet disinfecting cartridge that has a material that is highly absorptive of UVGI light such as zinc oxide that absorbs more than 95% of UVGI light, which will effectively reduce stray UV photons from exiting the outlet end of the cartridge tube.

An exemplary ultraviolet disinfecting cartridge may have an inlet and/or outlet filter that is configured to capture particles. The filter may include a filter material, such as a fabric, woven or non-woven, a screen or net. The filter material may be suitably permeable to enable airflow to pass therethrough. An exemplary filter material may by a HEPA filter and have a Frazier value of 20 or more, 50 or more, 100 or more and any range between and including the values provided. A filter may be configured to capture particles that are 2 microns or larger, 1 micron or larger, 0.75 microns or larger, 0.5 microns or larger and any range between and including the particle sizes provided. The filters may be detachably attachable so they can be replaced periodically to ensure optimal performance. The cartridge may have an access port that can be opened to remove the filter for replacement. When the access cover is opened, the controller may automatically shut the system off as a safety feature so that there is no escape opportunity for the UVGI light.

An exemplary ultraviolet disinfecting cartridge may have a flow assist fan configured to produce a flow of forced breathing air through the flow channel. The breathing air may be ambient air or may be air from a ventilator unit, which may be conditioned. Conditioned breathing air may have altered oxygen concentrations, controlled temperature and/or relative humidity and may be pressurized. An exemplary flow assist fan, which may be an axial or radial fan or other air moving device and may be configured proximal to the inlet of the flow channel. This forced flow of breathing air may be continuous and at a rate optimal for pathogen exposure time within the cartridge tube to ensure disinfection occurs at 99.9% or higher. The forced airflow may assist those with a compromised respiratory system with a reduced depth of breath by increasing the airflow and depth of breath entering the person's lungs.

An exemplary ultraviolet disinfecting cartridge may have a one-way exhale valve configured to exhaust breathing air when the pressure in the flow channel exceeds a threshold value to open the one-way flow valve. Breathing air may be the exhaled breathing air from the person donning the face mask. An exemplary one-way exhale valve may be configured proximal to the outlet of the flow channel, wherein the exhaled air may be at the greatest pressure. The pressure of the exhaled breathing air may be increased by the flow assist fan which may run continuously, or it may be pressure-activated. The one-way exhale valve may be configured to open only during exhaling, wherein the flow assist fan does not create sufficient pressure to restrict the exhaled breathing air passing through the valve.

An exemplary ultraviolet disinfecting cartridge may include an indicator to indicate the functions of the system, such as the activity of the UV lights, the activity of the ionizer, battery level and the like. An indicator may be an LCD screen and/or colored LED status indicators. The LCD may provide short text messages indicating status and error conditions. An audio signal may be included as part of the controller system. A user interface or switch may be used to turn on and off the various functions of the UV disinfecting cartridge, such as the UV lights and the ionizer.

An exemplary ultraviolet disinfecting cartridge system may be powered by a separate battery pack with a detachably attachable cable connecting the power source to the cartridge system on the face mask and patient ventilator embodiments. The battery pack may use chargeable or replaceable non-rechargeable batteries or both and the battery container may be designed for convenient storage on the user's body by a clasp or in a pocket. The battery pack may have an indicator showing the amount of power remaining or time remaining before running out of power, and an audio and/or LED light signal may also be on the pack. An internal battery system within the cartridge may be used if the power source is lightweight, but the system will likely require an external power source with a detachably attachable power cord.

An exemplary ultraviolet disinfecting cartridge system comprises an ultraviolet disinfecting cartridge particularly adapted for coupling with either a patient ventilator system and inserted along the inhale and/or exhale ventilator hoses or for coupling with a face mask device such as a commercial off the shelf face mask used with CPAP machines (Continuous Positive Airway Pressure) for persons with sleep apnea or other obstructive breathing problems. An exemplary face mask is a COTS ResMed Airfit F30 face mask, available from ResMed, San Diego, Calif. which is depicted in the figures and described in this application. This face mask and other similar to it that cover a user's mouth and nose are readily adapted to receive attachment devices such as the UV disinfecting cartridge either as a straight inline system or as a containerized system with a serpentine airflow channel. The ResMed AirTouch F20 face mask is another example of a full-face mask that could be used with the UV disinfecting cartridge. First responders and healthcare workers also use Personal Air Purifier Respirator (PAPR) Systems, which use industry standard tubing that may allow the UV disinfecting cartridge to be installed within the tubing line to provide disinfection through these portable systems as well.

An exemplary ultraviolet disinfecting cartridge system configured for attachment to a ventilator or along the ventilator hose may not have some of the features described herein, such as the flow assist fan, the one-way exhale valve, or the particle filters, for example because the patient ventilator has these features as part of its system. However, these features may be included for ultraviolet disinfecting cartridges adapted for a face mask wherein ambient air may be drawn through the ultraviolet disinfecting cartridge. The ultraviolet disinfecting cartridge may be configured as either a one-direction airflow system or a two-direction inhale and exhale airflow system. The ultraviolet disinfecting cartridge may be designed for forced airflow such as from a ventilator or it may be designed as a two-direction system where airflow is dependent on the inhaling and exhaling forces provided by the user's breathing.

The disinfection process may be more effective for airborne pathogens when airflow is controlled in a tubular system that has "kill zones" that meet the rate constant criteria for 99.9% disinfection. By adding more than one effective UV wavelength and an ionization system, the redundant disinfection means will yield more effective disinfection. This is because one UV wavelength is typically absorbed more readily by certain molecular structures in the pathogen than another UV wavelength.

Therefore, employing two UV wavelengths increases the opportunities for the pathogen to be neutralized or destroyed in a very short period of time when the pathogen is exposed because different vulnerable parts of its molecular structure are simultaneously targeted. In fact, absorption and molecular change at a vulnerable bond is nearly instantaneous when it occurs from a single UV light photon. Increasing the time of exposure ensures that all pathogens within the dispersion zone of the UV light receive a lethal neutralizing and/or destroying dose. Exposing airborne pathogens simultaneously to UV light, an ionizing system, and a small amount of ozone by-product within the kill zone multiplies the lethal effects ensuring disinfection is optimally effective at and above the 99.9% measure.

Pathogens are microbes that cause infections such as viruses, bacteria, and fungi. Allergens are microbes, biological products, and compounds that cause allergic reactions in individuals based on their genetic vulnerabilities. Most allergens are not susceptible to UV light, but an ionizing system along with at least one high efficiency particulate air (HEPA) filter included in the airflow of the cartridge disinfection system will remove most allergens. Removing allergens is a secondary benefit but is important as allergens can exacerbate a person's illness, especially in the respiratory system, which many pathogens typically infect people to some degree. Since this novel invention is primarily concerned with pathogen disinfection, the capability of the system to greatly reduce allergens from the cartridge airflow will only be briefly mentioned in this description. An exemplary ultraviolet disinfecting cartridge may be an effective air purifier by virtue of its effective removal of allergens, at a level of about 99.9% or more.

An exemplary ionizer system comprising an ionizer and ionizer collector bar destroys pathogens and helps collect allergens at the collector bar that removes particles from the air. Ionizing systems and UV disinfecting light also produce small amounts of ozone as a by-product. Ozone is an effective disinfectant. However, ozone may cause some people to have negative side effects from exposure. Hence, the ozone may be removed or reduced to safe levels by catalytic scrubbers at the end of the cartridge tube adjacent to the ionizer collector plates. In summary, an ionizing system and ozone by-product add to the disinfection effectiveness of the present novel invention, but the use of UV light is the primary means for disinfection.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 1:
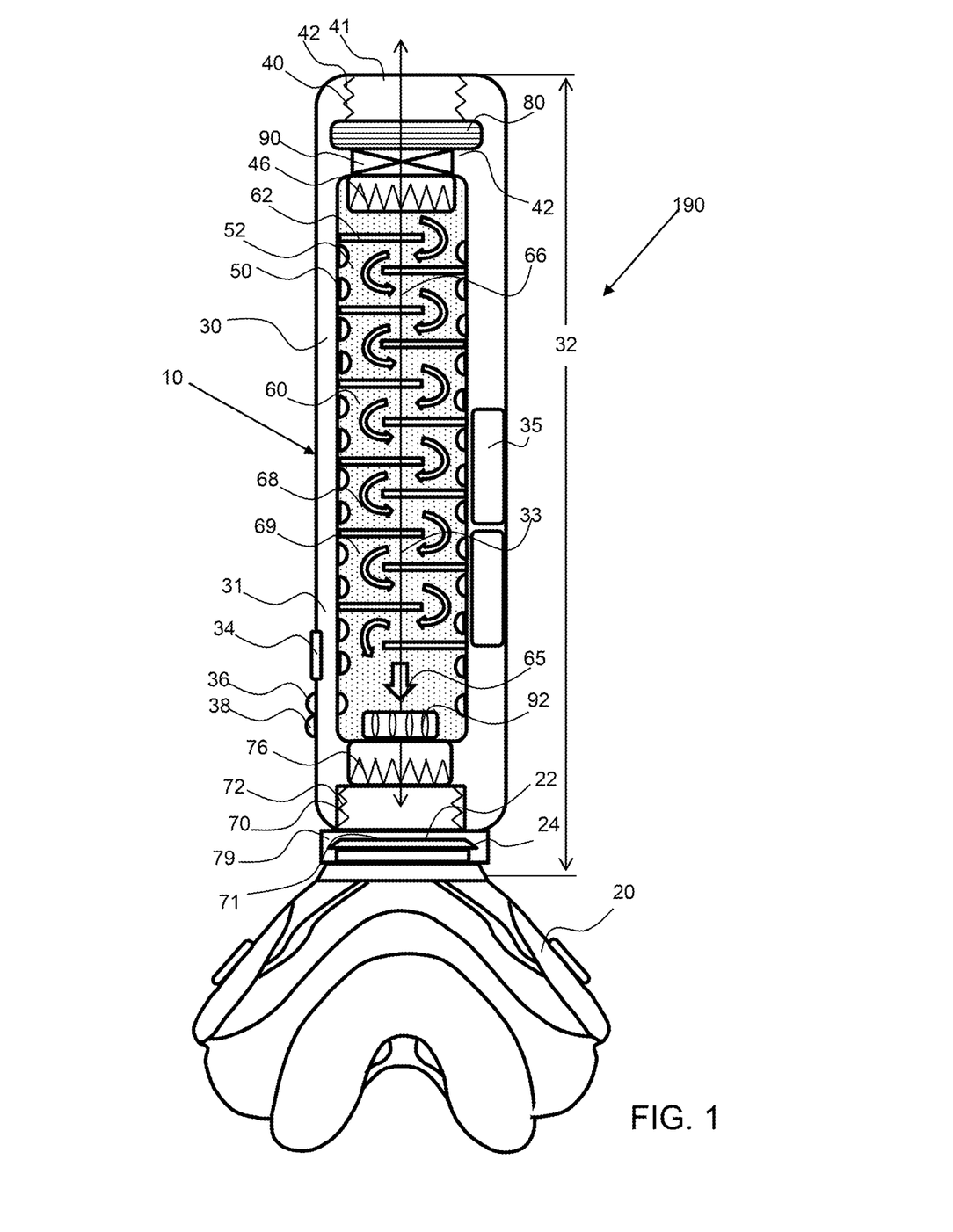
FIG. 1 shows an exemplary ultraviolet disinfecting cartridge coupled directly with an inlet opening on the front frame of a face mask and having a plurality of UV LED lights configured to emit UVGI light and an ionizing system for releasing charged particles into a flow channel to disinfect air breathed in and air exhaled out by the user and through the channel.

As shown in FIG. 1, an exemplary ultraviolet disinfecting cartridge face mask system 190 comprises an ultraviolet disinfecting cartridge system 10 including an ultraviolet disinfecting cartridge 30 that is coupled directly with an inlet 22 opening of a face mask 20 by an outlet adapter 70 on the front frame, which may comprise threads 72 for attachment with the face mask connector 24. Note that a face mask connector 24 may comprise a flange and the outlet adapter 70 of the ultraviolet disinfecting cartridge may be configured to press-fit over this flange to produce a connection that is effectively sealed. The ultraviolet disinfecting cartridge has an inlet 41 having an inlet adapter 40, which may have threads 42 for connection with a portable ventilator hose. The breathing air flows from the inlet 41, through the entire flow channel 60 to the outlet 71. The length 32 of the ultraviolet disinfecting cartridge may be effectively long to enable the UV light 52 emitted by the UV light emitters 50 to neutralize and/or destroy any pathogens flowing therethrough. A flow channel 60 may be configured with baffles 62 to create a tortuous path for the air flowing therethrough. This serpentine airflow path may increase the residence time of the disrupted air in the flow channel and thereby make disinfecting the air more effective. The baffles 62 may extend substantially orthogonal to the flow direction 65 to produce a serpentine flow along the flow channel. The baffles may produce a spiral flow through the flow channel as well, wherein the baffle spirals within the flow channel. An ultraviolet disinfecting cartridge 30 may include a plurality of UV light emitters 50 and they may be configured to emit light between the orthogonal baffles or into the flow channels 66 produced by the baffles. The flow channels are the space between the baffles that extend substantially orthogonal to the length axis 33 of the ultraviolet disinfecting cartridge. Substantially orthogonal to the length axis means at least 65 degrees offset from the length axis, or at least 75 degrees offset, and up to 90 degrees offset, wherein 90 degrees offset is orthogonal to the length axis. The exemplary ultraviolet disinfecting cartridge has a length 32 from the inlet 41 to the outlet 71.

An exemplary ultraviolet disinfecting cartridge may also include a reactive material 68, such as a catalyst 69. A reactive material may react with compounds in the breathing or exhalation air to destroy them. For example, titanium dioxide may be configured within the flow channel to react with volatile organic compounds and pathogens in the presence of UV light. Another catalyst, such a manganese dioxide may be configured to react with ozone to reduce or eliminate ozone that may be included in the breathing air. An ionizer 80 may be coupled with the ultraviolet disinfecting cartridge proximal to the inlet 41 to ionize air in the flow channel to provide disinfection and it produces ozone as a by-product. This ozone may also react with pathogens to destroy or neutralize them. A reactive compound 68 or catalyst 69 may be configured on surfaces within the flow channel, such as the interior wall of the flow channel and/or on the baffle surfaces. The reactive material may be configured more proximal to the outlet 71 of the ultraviolet disinfecting cartridge or flow channel to provide enough resonance time for reaction with pathogens and allergens. Ionizer collector bars 92 may also be installed in the flow channel before the outlet filter 76 to remove ionized particulates.

Figure 4:
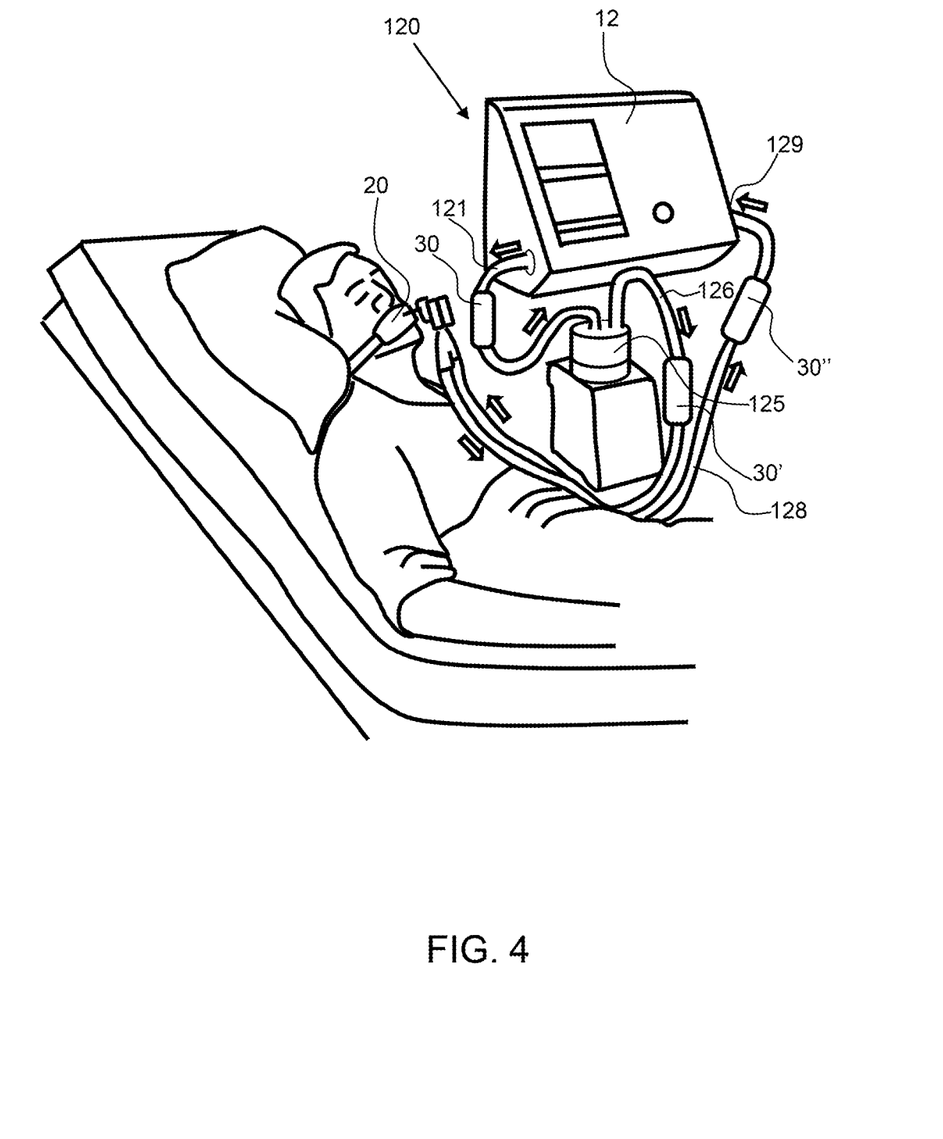
FIG. 4 shows an exemplary ultraviolet disinfecting cartridge system for a patient ventilator system comprising an ultraviolet disinfecting cartridge coupled with the inhale and exhale ventilator hoses to disinfect inhaled air and exhaled air that is released into the patient's room where it might infect healthcare workers.

Also shown in FIG. 1, an exemplary ultraviolet disinfecting cartridge may comprise an inlet filter 46 and/or an outlet filter 76 to capture and collect particles. These filters may include a filter material allowing an effectively high airflow to not restrict the flow of breathing air to the patient. An exemplary ultraviolet disinfecting cartridge system will not cause any significant restriction in air flow that may cause the user to have to work or feel uncomfortable breathing in and out when using the ultraviolet disinfecting cartridge system 10 or patient ventilator 12 as shown in FIG. 4. The filter material may have a permeability of 20 Frazier or more, 40 Frazier or more, 80 Frazier or more, 150 Frazier or more and any range between and including the permeability values provided. The inlet or outlet filter may include pleated filter material to increase the amount of filter surface area and to further decrease the pressure drop through the filter. The filter material may be a non-woven, a membrane, a woven material or screen such as a HEPA filter. The inlet or outlet filters may be detachably attachable, wherein they can be periodically removed and replaced with a new filter.

An exemplary ultraviolet disinfecting cartridge may comprise an indicator 36 to indicate the function of lights and/or the ionizer, or battery level. An indicator may be a display screen 34, such as an LCD screen. A user input 38 may be used to activate and deactivate the lights and or the ionizer. One or more batteries 35 may be used to power the ultraviolet disinfecting cartridge functions and the indicator 36 may display the battery power level. An indicator may be a light configured on the cartridge housing 31 and may flash or change color when the battery state of charge is below a threshold level.

Also shown in FIG. 1 is a flow assist fan 90 or air moving device configured to force breathing air into the flow channel. This may help patients on ventilators or those donning the ultraviolet disinfecting cartridge 30 to inhale more easily, especially those with compromised breathing functions. The breathing air, which may be from ambient air or from a ventilator may be forced down through the flow channel 60, around the baffles 62 and through the face mask 20 for breathing. A one-way exhale valve 79 may be configured to enable exhaled air to escape from the system. The flow assist fan 90 may be configured proximal to the inlet 41 and the one-way exhale valve 79 may be configured proximal to the outlet 71, as shown.

As described herein, some of the features shown in FIG. 1 may not be included in an ultraviolet disinfecting cartridge 30 when it is adapted for coupling with a ventilator or ventilator hose, wherein the breathing air is provided from a ventilator as shown in FIG. 4. A ventilator may have a flow of breathing air that is pre-filtered and may be provided under pressure wherein a flow assist fan 90, and filters 46, 76 are not required.

The ultraviolet disinfecting cartridge system 10 as shown in FIG. 1 may be an effective air purifier and remove allergens through filtration by the inlet filter 46, outlet filter 76 and/or the ionizer system comprising the ionizer 80 and ionizer collector bar 92. The ultraviolet disinfecting cartridge 30 may remove up to about 99.9% of allergens.

Figure 2:
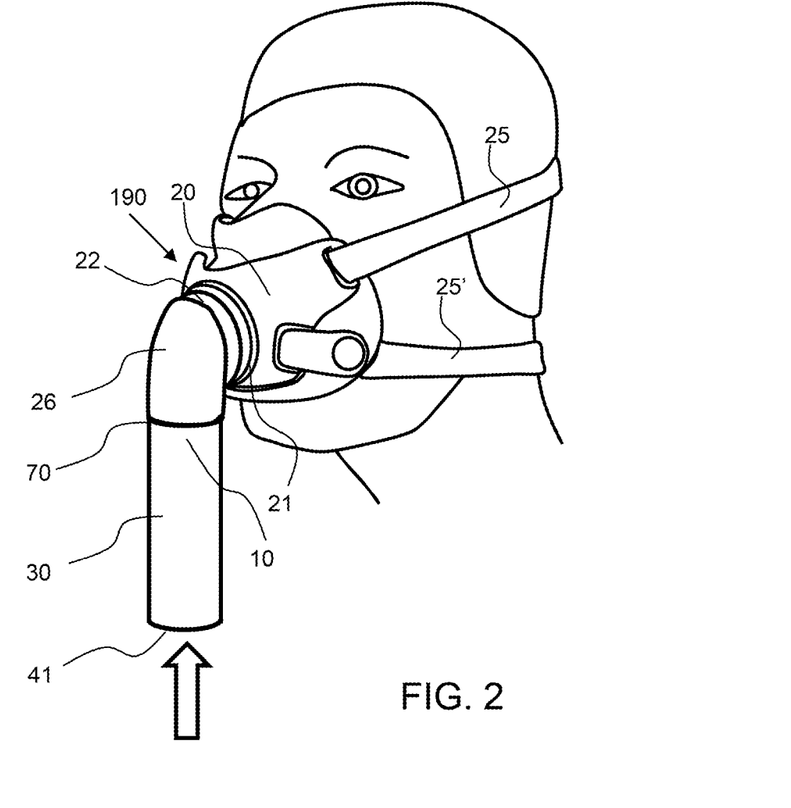
FIG. 2 shows a person wearing a straight inline ultraviolet disinfecting cartridge face mask system coupled by an elbow adaptor that swivels on the front of a face mask.

As shown in FIG. 2, an ultraviolet disinfecting cartridge system 10 comprises an exemplary ultraviolet disinfecting cartridge 30 coupled with the face mask 20. An elbow 26 swivels and is part of the face mask assembly 21 and is coupled with the inlet 22 of the face mask. The ultraviolet disinfecting cartridge 30 is coupled with the elbow 26 via the adapter 70. The ultraviolet disinfecting cartridge has an inlet 41 that draws air into the cartridge flow channel. The inlet 41 has an adapter configured to couple with an external ventilator hose and an outlet adapter 70 configured to couple with the elbow, or directly with the face mask connector 24, as shown in FIG. 1. As air passes through the cartridge flow channel as shown in FIG. 1, UV light is emitted within the ultraviolet disinfecting cartridge to neutralize or destroy any pathogens flowing through the air in the ultraviolet disinfecting cartridge that is then breathed in by the user. The ultraviolet disinfecting cartridge 30 may be configured to swivel or rotate about the coupling with the face mask or with the elbow 26 of the face mask. The elbow may be configured to rotate or swivel to allow the UV disinfecting cartridge 30 some freedom of movement so that it can deflect away from an object to avoid the possibility of the air seal being broken with the face mask attached around a user's nose and mouth. Finally, the face mask creates a seal with the user's face by adjusting a set of detachably attachable straps 25, 25' that are configured around and over the user's head.

Figure 3:
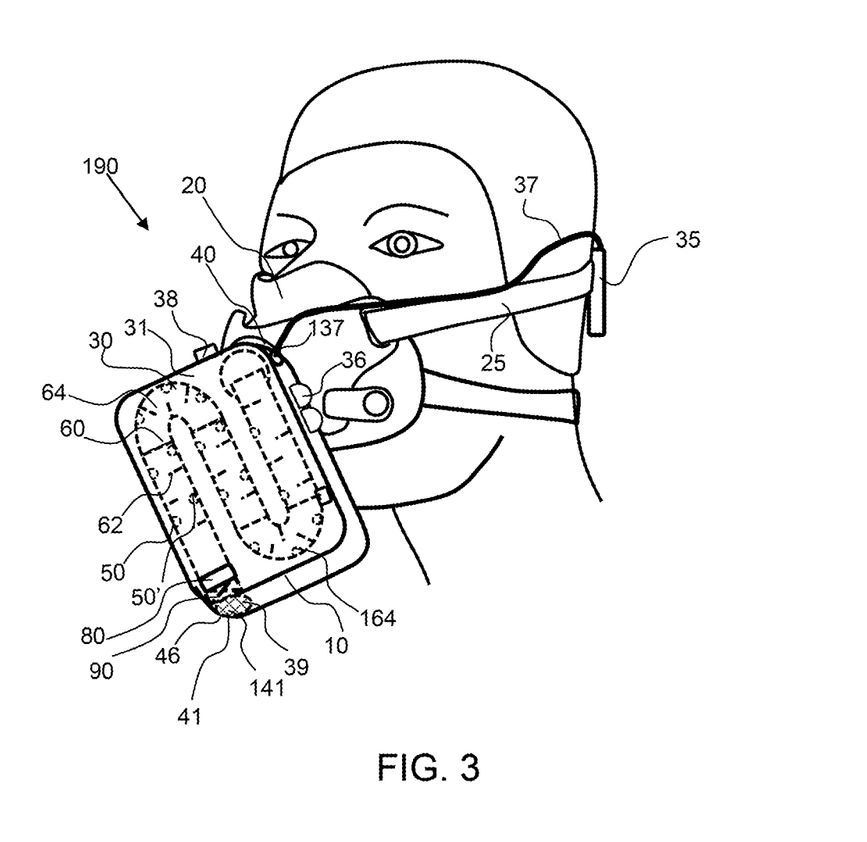
FIG. 3 shows a person wearing a containerized UV disinfecting cartridge that has a serpentine design where the cartridge flow channel makes two 180-degree turns, which comprises a separate face mask embodiment that can be attached to the face mask onto either the front frame or onto the elbow adaptor that allows the cartridge to swivel during use to disinfect inhaled and exhaled air breathed through the flow channel.

As shown in FIG. 3, the UV disinfecting cartridge system 10 comprises a face mask 20 and an exemplary UV disinfecting cartridge 30 contained in a cartridge housing 31 where the flow channel 60 serpentines within the housing having at least two 180-degree bends 164 in the serpentine UV disinfecting cartridge 64. This allows the UV disinfecting cartridge to be more compact and closer to the face mask 20, which is more ergonomic than the inline UV disinfecting cartridge shown in FIG. 2, as it is less obstructive, and the weight distribution is better balanced for the user. The exemplary UV disinfecting cartridge 30 has a user input 38 to control function of the UV disinfecting cartridge including turning the cartridge on and off, controlling operating modes where one, a first and/or second UV light emitters 50, 50' are turned on, and turning on the ionizer 80. As described herein a first UV light emitter 50 may produce a first wavelength of UV light and a second UV light emitter 50' may produce a second wavelength of UV light that is substantially different than the first wavelength of UV light, or at least 10 nm different. The UV disinfecting cartridge also has an inlet UV screen 141 that blocks stray UV light from escaping through the inlet housing, and an inlet filter 46 in a filter housing 39 to capture and retain particles before they enter the airflow channel. An exemplary UV disinfecting cartridge 30 also has a fan 90 that produces a continuous, regulated airflow in the flow channel baffles 62 that disrupt the airflow and increase the exposure time of airborne pathogens to the disinfecting UV light and ionizer.

As shown in FIG. 3, an exemplary UV disinfecting cartridge face mask system 190 comprises a UV disinfecting cartridge system 10 that comprises a detachably attachable power cord 37 that connects to the cartridge housing by a battery cord port 137, such as a USB port. A separate battery power pack may be attached to the face mask 20, such as to the back of the straps on the face mask to better balance the weight distribution between the battery pack and the UV disinfecting cartridge. The battery power cord may attach to the straps 25 that secure the face mask 20 to the user's face to enclose and seal the user's nasal and mouth areas.

As shown in FIG. 4, an exemplary ventilator system 120 comprises a ventilator 12 and a humidification portion 125. One or more exemplary UV disinfecting cartridges 30, 30', 30" are inserted and coupled with a patient ventilator system. A first exemplary UV disinfecting cartridges 30 is configured between the outlet hose 121 of the outlet of the ventilator and the humidification portion 125. A second exemplary UV disinfecting cartridges 30' is configured between the humidification portion and the face mask 20 or along the inhale hose. A third exemplary UV disinfecting cartridges 30" is configured between the face mask and the return port 129 of the ventilator 12 or along the exhale hose 128. These one or more UV disinfecting cartridges 30 ensures that inhaled air is disinfected before entering the patient and the exhaled air from the patient, which may likely include a pathogen "load" that could easily infect healthcare workers or personal visitors in the healthcare facility room, is also disinfected. The UV disinfecting cartridge in the exhale tubing also eliminates the need for the infected patient on a ventilator to be housed in a room where a positive pressure airflow system specific to the room is installed. Note that the UV disinfecting cartridge intended for patient ventilator systems in a healthcare facility, as shown in FIG. 4, may have some or all of the features of the UV disinfecting cartridge shown in FIG. 1 or 2. The UV disinfecting cartridge used with the ventilator system 120 may not require some of the components in the UV disinfecting cartridge configured for use with a face mask, such as the airflow assist fan, inlet and outlet filters, and one-way exhale valves that allow exhaled air to flow back through the flow channel. In effect, the primary means and methods of disinfection in the novel face mask and ventilator embodiments described in this application are the same.

It will be apparent to those skilled in the art that various modifications, combinations, and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An ultraviolet disinfecting cartridge system comprising:
   an ultraviolet disinfecting cartridge comprising:
   a) a flow channel extending from an inlet to an outlet for receiving a flow of breathing air and comprising an interior surface that has dimples;
       wherein the inlet and the outlet are aligned along a length axis of the ultraviolet disinfecting cartridge;
   b) a UV light emitter configured along said interior surface of the flow channel and configured to emit ultraviolet light into the flow channel;
   c) an inlet adapter configured to couple with a ventilator hose;
   d) an outlet adapter configured to couple directly with an inlet opening of a face mask;
   e) an inlet filter configured proximal to the inlet of the flow channel;
   f) an outlet filter configured proximal to the outlet of the flow channel;
   g) an ionizer that emits charged particles and is configured proximal to the inlet of the flow channel;
   h) an ionizer collector configured proximal to the outlet of the flow channel that removes charged particles from the flow of breathing air;
       wherein the ionizer collector is detachably attachable to the ultraviolet disinfecting cartridge;
   i) a reactive material configured in the flow channel, said reactive material comprising a photocatalyst configured to react with pathogens in the presence of the ultraviolet light emitted by the UV light emitters to increase pathogen disinfection;
   j) six or more baffles extending from the interior surface of the flow channel substantially orthogonal to the length axis of the ultraviolet disinfecting cartridge to produce orthogonal flow channels within the flow channel to increase the resonance time of the flow of breathing air from the inlet to the outlet;
   k) a flow assist fan configured to produce said flow of breathing air through the flow channel and wherein the flow assist fan is configured proximal to the inlet of the flow channel;
   wherein a portion of the plurality of UV light emitters are configured within the orthogonal flow channels and configured to emit ultraviolet light into the orthogonal flow channels;
   wherein a first UV light emitter of the plurality of UV light emitters emits a first UV light having a narrow band wavelength of 220 nm +/−5 nm to neutralize pathogens and a second UV light emitter of the plurality of UV light emitters emits a second UV light having a second wavelength between 250 nm and 280 nm to destroy pathogens;
   wherein the UV light is configured to destroy or neutralize pathogens in said flow of breathing air;
   wherein the dimples on the interior surface are configured to produce a random dispersion of reflected UV light; and
   wherein the ultraviolet disinfecting cartridge system has an allergen removal efficiency of 99.9% or more air purification;
   wherein the ultraviolet disinfecting cartridge system utilizes a combination of two UV wavelengths, ionization and ozone by-product to achieve a disinfection of 99.9% or more of pathogens.

2. The ultraviolet disinfecting cartridge system of claim 1, wherein the baffles comprise a dimpled surface configured to create a random dispersion of reflected ultraviolet light from said UV light emitters.

3. The ultraviolet disinfecting cartridge system of claim 1, wherein the photocatalyst is titanium dioxide.

4. The ultraviolet disinfecting cartridge system of claim 1, wherein the reactive material is a catalyst configured proximal to the outlet of the ultraviolet disinfecting cartridge that is configured to react with ozone in the airflow channel to reduce ozone to a level of no more than 1.0 ppm.

5. The ultraviolet disinfecting cartridge system of claim 4, wherein the ozone reactive material is manganese dioxide.

6. The ultraviolet disinfecting cartridge system of claim 1, wherein the inlet filter and the outlet filter are detachably attachable.

7. The ultraviolet disinfecting cartridge system of claim 1, further comprising:
   an indicator to indicate the type of UV light being emitted.

8. The ultraviolet disinfecting cartridge system of claim 7, further comprising a user input to change the type and amount of UV light being emitted and whether the ionizer is on or off.

9. The ultraviolet disinfecting cartridge system of claim 1, further comprising an indicator screen to indicate that the ionizer system is operating and further comprising an indicator to indicate the battery level of the batteries.

10. The ultraviolet disinfecting cartridge system of claim 1, further comprising a flow assist fan configured to produce a continuous and regulated flow of positive pressure airflow through the flow channel and wherein the flow assist fan is configured proximal to the inlet of the flow channel.

11. The ultraviolet disinfecting cartridge system of claim 1, further comprising:
  a one-way exhale valve configured adjacent to the flow channel of the ultraviolet disinfecting cartridge to exhaust breathing air when the pressure in the flow channel exceeds a threshold value to open the one-way exhale valve.

12. The ultraviolet disinfecting cartridge system of claim 11, wherein the one-way exhale valve is configured proximal to the outlet of the flow channel.

13. The ultraviolet disinfecting cartridge system of claim 1, comprising:
  a first ultraviolet disinfecting cartridge and a second ultraviolet disinfecting cartridge, each comprising:
   a) a flow channel extending from an inlet to an outlet for receiving a flow of breathing air;
   b) a UV light emitter configured to emit ultraviolet light into the flow channel;
   c) an inlet adapter configured to couple with a ventilator hose;
   d) an outlet adapter configured to couple with a face mask;
  wherein the UV light is configured to destroy or neutralize pathogens in said flow of breathing air;
   a face mask wherein said first ultraviolet disinfecting cartridge is coupled with the face mask;
   a ventilator comprising an outlet hose and an exhale hose, and wherein the face mask is a ventilator face mask and wherein said outlet hose extends from the first ultraviolet disinfecting cartridge to said ventilator; and
   wherein the first ultraviolet disinfecting cartridge is configured between said face mask and said ventilator;
   a second ultraviolet disinfecting cartridge configured between the face mask and the ventilator and coupled with the exhale hose, downstream of the first ultraviolet disinfecting cartridge and between the first ultraviolet disinfecting cartridge and the ventilator.

* * * * *